(12) United States Patent
Derkx et al.

(10) Patent No.: US 11,083,404 B2
(45) Date of Patent: Aug. 10, 2021

(54) PROCESSING APPARATUS FOR PROCESSING A PHYSIOLOGICAL SIGNAL

(71) Applicant: KONINKLIJKE PHILIPS N.V., Eindhoven (NL)

(72) Inventors: Rene Martinus Maria Derkx, Eindhoven (NL); Sandrine Magali Laure Devot, Cologne (DE); Jakob Van De Laar, Oosterhout (NL)

(73) Assignee: Koninklijke Philips N.V., Eindhoven (NL)

( * ) Notice: Subject to any disclaimer, the term of this patent is extended or adjusted under 35 U.S.C. 154(b) by 335 days.

(21) Appl. No.: 16/314,187

(22) PCT Filed: Jun. 26, 2017

(86) PCT No.: PCT/EP2017/065641
§ 371 (c)(1),
(2) Date: Dec. 28, 2018

(87) PCT Pub. No.: WO2018/001929
PCT Pub. Date: Jan. 4, 2018

(65) Prior Publication Data
US 2019/0320930 A1   Oct. 24, 2019

(30) Foreign Application Priority Data

Jun. 30, 2016 (EP) .................................. 16177067

(51) Int. Cl.
*A61B 5/389* (2021.01)
*A61B 5/30* (2021.01)
*A61B 5/00* (2006.01)

(52) U.S. Cl.
CPC ................ *A61B 5/389* (2021.01); *A61B 5/30* (2021.01); *A61B 5/6801* (2013.01)

(58) Field of Classification Search
CPC ........... A61B 5/28; A61B 5/296; A61B 5/308; A61B 5/313; A61B 5/318–366; A61B 5/389–397; A61B 5/0803
See application file for complete search history.

(56) References Cited

U.S. PATENT DOCUMENTS 4,248,240 A * 2/1981 van Eykern ......... A61B 5/0809
600/484
7,221,975 B2 * 5/2007 Lindstrom ......... G06K 9/00503
600/509

(Continued)

FOREIGN PATENT DOCUMENTS

WO     2005096924 A1    10/2005
WO  WO-2015044010 A1 *  4/2015 ............. A61B 5/113

OTHER PUBLICATIONS

A. Bartolo et al., Analysis of diaphragm EMG signals: comparison of dating vs. subtraction for removal of ECG contamination, Journal of Applied Physiology, 80(6), pp. 1898-1902, Jun. 1996.

(Continued)

*Primary Examiner* — Thaddeus B Cox
(74) *Attorney, Agent, or Firm* — Daniel H. Brean

(57) ABSTRACT

A processing apparatus for processing a physiological signal using model subtraction, notch filtering and gating. The processing apparatus comprises a model subtraction circuit configured to receive the physiological signal and to reduce a first unwanted signal component, such as an ECG contamination, in the physiological signal by subtracting from the physiological signal a model of the first unwanted signal component to obtain a residual signal; a filter circuit configured to receive the residual signal and to reduce a second unwanted signal component, such as power line noise, in the residual signal by applying a notch filter to obtain a filtered signal; and a gating circuit configured to receive the filtered signal and to apply gating to the filtered signal to obtain a (Continued)

gated signal. The processing apparatus further relates to a corresponding electromyography system and a method for processing a physiological signal using model subtraction, notch filtering and gating.

18 Claims, 8 Drawing Sheets

(56) References Cited

U.S. PATENT DOCUMENTS

| | | | |
|---|---|---|---|
| 7,623,912 B2 | 11/2009 | Solange et al. | |
| 2005/0125473 A1 | 6/2005 | Lindstrom | |
| 2006/0155386 A1* | 7/2006 | Wells | A61B 5/389 623/25 |
| 2006/0235315 A1* | 10/2006 | Akselrod | A61B 5/389 600/509 |
| 2010/0087900 A1* | 4/2010 | Flint | A61B 5/1101 607/104 |
| 2013/0213399 A1 | 8/2013 | Hansmann et al. | |
| 2013/0310699 A1* | 11/2013 | Hart | A61B 5/0205 600/484 |
| 2014/0073948 A1 | 3/2014 | Engelbrecht et al. | |
| 2014/0142395 A1* | 5/2014 | Sattler | A61B 5/0205 600/300 |
| 2014/0240103 A1 | 8/2014 | Lake et al. | |
| 2015/0126821 A1 | 5/2015 | Kempfner et al. | |
| 2016/0113586 A1* | 4/2016 | Hemming | A61B 5/318 600/510 |
| 2016/0220850 A1 | 8/2016 | Tyler | |
| 2016/0228069 A1 | 8/2016 | Derkx et al. | |
| 2018/0020928 A1 | 1/2018 | Hart et al. | |

OTHER PUBLICATIONS

Drake, J.D.M.et al., "Elimination of electrocardiogram contamination from electromyogram signals: A evaluation of currently used removal techniques", Journal of Electromyogaphy and Kinesiology, Elsevier, Amsterfdam, N>, vol. 16, No. 2, Apr. 1, 2006, pp. 175-187.

Ragupathy S. C. et al., "Electrocardiogram removal from electrmyogram of the muscles", Proceedings of the 26th Annual International Conference of the IEEE EMBS, San Francisco, CA, vol. 3, Sep. 1, 2004, pp. 243-246. vol. 1.

Lu, G. et al., "Removing ECG noise from surface EMG signals using adaptive filtering", Neuroscience Letters, Elsevier, Amsterdam, NL, vol. 462, No. 1, Sep. 18, 2009, pp. 14-19.

Nitzken, M. et al., "Local wavelet-based filtering of electromyographic signals to eliminate the electrocardiographic-induced artifacts in patients with spinal cord injury", Journal of Biomedical Science and Engineering, vol. 6, No. 7, Jan. 1, 2013, pp. 1-13.

Willigenburg, N.W. et al., "Removing ECG contamination from EMG recordings: A comparison of ICA-based and other filtering procedures", Journal of Electromyography and Kinesiology, Elsevier, Amsterdam, NL, vol. 22, No. 3, Jan. 3, 2012, pp. 485-493.

Murphy, P.B. et al., "Chronic obstructive pulmonary disease, Neural respiratory drive as a physiological biomarker to monitor change during acute exacerbations of COPY", Thorax 2010, May 19, 2011.

Breslin, E.H., "Respiratory muscle function in patients with chronic obstructive pulmonary disease", Heart & Lung, vol. 24, No. 4, Jul./Aug. 1996, pp. 271-285.

Duiverman, M.L., et.al., "Reproducibility and responsiveness of a non-invsaive EMG technique of the respiratory muscles in COPD patients and in healthy subjects", J. Appl. .Physiol., Dec. 5, 2003.

De Troyer, A., et. al., "Respiratory Action of the Intercostal Muscles", Physiol Rev, vol. 85, pp. 717-756, 2005.

Han, J.N., et. al., "Respiratory function of the rib cage muscles," Eur Respir J, vol. 6, pp. 722-728, 1993.

Pan, J. et al. "A real-time QRS detection algorithm", IEEE Trans. Biomed. Eng., vol. 32, No. 3, pp. 230-236, 1985.

Hamilton, P.S., "A Comparison of Adaptive and Nonadaptive Filters for Reduction of Power Line Interference in the ECG", IEEE Transaction on Biomedial Engineering, vol. 43, No. 1, Jan. 1996.

Van Eykern, L. et al. Two similar averages for respiratory muscle activity, Letter to editor, J. Appl. Physiology 90:2014-2015, 2001.

Mewett, D.T., et.al., "Reducing power line interference in digitized electromyogram recordings by spectrum interpolation", Med. Biol. Eng. Comput., 2004, 42, 524-531.

\* cited by examiner

PROCESSING APPARATUS FOR PROCESSING A PHYSIOLOGICAL SIGNAL

This application is a national stage application under 35 U.S.C. § 371 of International Application No. PCT/EP2017/065641 filed on Jun. 26, 2017 and published in the English language on Jan. 4, 2018 as International Publication No. WO 2018/001929, which claims priority to European Patent Application No. 16177067.2 filed on Jun. 30, 2016, the entire disclosures of which are incorporated herein by reference.

FIELD OF THE INVENTION

The present invention relates to the field of medical technology and signal processing. In particular, the present invention relates to a processing apparatus for processing a physiological signal using model subtraction, notch filtering and gating. The present invention further relates to a corresponding system and method as well as to a corresponding computer program for carrying out said method.

BACKGROUND OF THE INVENTION

Removal of unwanted signals from a measured signal is a commonly known action in signal processing. One application involving such action is the processing of electromyography (EMG) signals.

Electromyography is a technique for determining an activity of a muscle or a group of muscles. An electromyography system detects an electrical potential generated by muscle cells when these cells are electrically or neurologically activated. Two or more electrodes are applied to obtain a differential voltage signal indicative of an activity of the muscle.

Signals can either be measured directly within the muscle (invasive EMG) or on the skin above the muscle (surface EMG). For invasive EMG, two electrodes are directly inserted into the muscle tissue of interest. For surface EMG, as a non-invasive technique, two electrodes are applied to the skin of the subject.

Surface EMG measurements involve the detection, processing and recording of very small electrical variations generated by muscle tissue. For small muscles like intercostal muscles, these signals are often only a few microvolts in amplitude and can therefore be subject to interference from other more dominant noise sources, either from the measurement system, external influences, or from the human body itself.

In patients with chronic obstructive pulmonary disease (COPD) and other respiratory diseases, the assessment of a parasternal muscle activity, for example measured from surface EMG with electrodes positioned at the second intercostal space, can be useful to estimate an intensity, timing and duration of a patient's respiratory effort. This can serve as an indicator of the balance between respiratory muscle load and respiratory muscle capacity. A maximum EMG level that occurs during inhalation is related to the neural respiratory drive (NRD). In COPD patients during increasing lung hyperinflation as observed during acute exacerbation, there is a change in the balance between respiratory muscle load and capacity, which is reflected by the neural respiratory drive. A lower capacity and a higher load can result in an increased NRD.

WO 2005/096924 A1 discloses an electrical device which may be used for monitoring and processing of a diaphragmatic electromyogram signal as an indicator of inspiratory effort. The solution disclosed therein intends to improve upon the current use of diaphragmatic electromyogram signals in the diagnosis of sleep disorders by eliminating contaminant electrocardiogram (ECG) signals. For this purpose, a filter stage comprising a notch filter is provided which is followed by an ECG (EKG) blanker configured to receive a blanking pulse and to remove an electrocardiogram (ECG) signal from the electromyogram (EMG) signal during said blanking pulse.

US 2014/0073948 A1 discloses a physiological monitoring system that may process a physiological signal such a photoplethysmograph signal from a subject. The system may determine physiological information, such as a physiological rate, from the physiological signal. The system may use search techniques and qualification techniques to determine one or more initialization parameters. The initialization parameters may be used to calculate and qualify a physiological rate. The system may use signal conditioning to reduce noise in the physiological signal and to improve the determination of physiological information. The system may use qualification techniques to confirm determined physiological parameters. The system may also use autocorrelation techniques, cross-correlation techniques, fast start techniques, and/or reference waveforms when processing the physiological signal.

Drake et al., "Elimination of electrocardiogram contaminations from electromyography signals: An evaluation of currently used removal techniques", Journal of Electromyography and Kinesiology 16, pp. 175-187, 2006 refers to different techniques for removal of ECG contaminations in EMG measurements.

Ragupathy, et al., "Electrocardiogram Removal from Electromyogram of the Lumbar Muscles", Proceedings of the 26th Annual International Conference of the IEEE EMBS, pp. 243-246, 2004 teaches ECG artifact removal from EMG measurements of the lumbar muscles using an independent component analysis (ICA) technique.

SUMMARY OF THE INVENTION

It is an object of the present invention to provide a processing apparatus and method for processing a physiological signal with improved performance. It would be particularly advantageous to reduce contributions from unwanted signal components in a physiological signal, in particular to reduce power line noise and contaminant electrocardiogram (ECG) signals.

In a first aspect of the present invention, a processing apparatus for processing a physiological signal using model subtraction, notch filtering and gating is presented. The processing apparatus comprises:

a model subtraction unit configured to receive the physiological signal and to reduce a first unwanted signal component in the physiological signal by subtracting from the physiological signal a model of the first unwanted signal component to obtain a residual signal;

a filter unit configured to receive the residual signal and to reduce a second unwanted signal component in the residual signal by applying a notch filter to obtain a filtered signal; and a gating unit configured to receive the filtered signal and to apply gating to the filtered signal to obtain a gated signal.

In a further aspect of the present invention, an electromyography system is presented that comprises two electrodes for application to a skin of a subject for acquisition of a physiological signal; and the afore-mentioned signal processing apparatus for processing said physiological signal using model subtraction, notch filtering and gating.

In a further aspect of the present invention, a method for processing a physiological signal using model subtraction, notch filtering and gating is presented. The method comprises the steps of:

reducing a first unwanted signal component in the physiological signal by subtracting from the physiological signal a model of the first unwanted signal component to obtain a residual signal;

subsequently reducing a second unwanted signal component in the residual signal by applying the notch filter to obtain a filtered signal; and subsequently applying gating to the filtered signal to obtain a gated signal.

In yet further aspects of the present invention, there are provided a corresponding computer program which comprises program code means for causing a computer to perform the steps of the method disclosed herein when said computer program is carried out on a computer as well as a non-transitory computer-readable storage medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed system, in particular as defined in the dependent claims and as disclosed herein.

The herein presented solutions provide a possibility to improve the performance of a signal processing apparatus. In particular, contributions from unwanted signal components as well as potential artifacts that are introduced by the signal possessing itself may be reduced. This can be particularly advantageous to reduce power line noise and contaminant electrocardiography (ECG) signals in a measured electromyography (EMG) signal.

The present invention is based on an idea to provide an advantageous combination of model subtraction, notch filtering and gating, more specifically to combine model subtraction and gating and placing a notch filter in between. For better understanding, the invention will be explained in the following with reference to the non-limiting example of removing power line noise and a contaminant ECG signal component from an EMG signal.

At first glance, it may seem counterintuitive to also apply model subtraction if a subsequent gating step is applied anyway. However, the specific sequence of model subtraction followed by a filter unit with a notch filter followed by a gating unit has been found to provide an advantageous outcome.

The present invention suggests to provide a model subtraction unit configured to receive the physiological signal and to reduce a first unwanted signal component in the physiological signal by subtracting from the physiological signal a model of the first unwanted signal component to obtain a residual signal as the first step, which is then followed by a filter unit comprising a notch filter and a gating unit as the subsequent steps.

In an exemplary scenario, it would be desirable to determine an inspiratory respiratory effort from EMG signals measured via two EMG electrodes, for example, located at a second intercostal space. The desired EMG signal from the parasternal muscles is a rather weak signal, because the parasternal muscles are small muscles. The EMG signal may suffer from power line noise, i.e., 50 Hz or 60 Hz sinusoidal noise as an unwanted signal component. In particular, the problem of power line noise can occur in equipment where there is an impedance mismatch between the electrodes and/or cables going to the differential amplifier stage. Such a mismatch can be due to poor shielding of the cables and/or poorly mounted electrodes. The first can occur when cost-effective equipment is used and the second can occur, for example, when the person applying the electrodes such as EMG electrodes is less experienced. Both situations can arise in a home care scenario where a COPD patient at home needs to measure an inspiratory EMG activity. In contrast to hospital equipment, the home equipment should be low-cost. Moreover, the COPD patient himself and/or a health coach needs to take care of the application of the EMG electrodes instead of highly trained health professionals at a hospital or other medical care facility.

Power line noise can be effectively reduced from a measured signal by applying a notch filter. For the case of an EMG signal there can be a spectral overlap between the desired EMG signal and power line noise in the 50 Hz and/or 60 Hz regions. It would thus be desirable to keep the notch filter as sharp as possible. For example, in the case of 50 Hz power line noise it would be desirable to have a sharp notch filter that has a −3 dB points stretching from 49 Hz up to 51 Hz.

In addition to power line noise, the measured EMG signal may also suffer from a high level of ECG contamination as a further unwanted signal component. For example, an R-peak of a QRS-complex of the ECG contamination can have a much larger amplitude compared to the respiratory EMG activity. The term "QRS complex" as used herein can refer to a portion of an ECG signal representing the actual successive atrial/ventricular contraction of the heart. It has been found that in the scenario of having a much larger ECG peak compared to the inspiratory EMG activity a sharp notch filter can give rise to so-called ringing artifacts due to a large group-delay of the filter. The ringing artifacts can lead to additional harmonics which can result in additional capping of the signal during the subsequent gating step, because the additional harmonics represent energy and the gating step may be configured to cap the signal components exceeding a certain threshold. Hence, a subsequent ECG suppression by gating may not work sufficiently well and result in reduced coverage of the respiratory EMG activity.

The proposed arrangement of providing the filter unit comprising the notch filter in between the model subtraction and the gating effectively overcomes this drawback. Furthermore, ringing artifacts introduced by a sharp notch filter can be reduced.

The measured physiological signal can comprise a desired EMG signal, a first unwanted signal component such as an unwanted ECG signal component, and a second unwanted signal component, in particular a periodic unwanted signal component such as power line noise. The proposed model subtraction unit receives this physiological signal comprising the unwanted signal components and determines a model signal or model of the first unwanted signal component, as for example described in WO 2015/044010 A1. This model of the first unwanted signal component is then subtracted from the received physiological signal to reduce the first unwanted signal component in the physiological signal. For details of an exemplary model subtraction reference is made to WO 2015/044010 A1, a prior patent application of the applicant, and A. Bartolo et al., "Analysis of diaphragm EMG signals: comparison of gating vs. subtraction for removal of ECG contamination", Journal of Applied Physiology, 80(6), pp. 1898-1902, June 1996, which are incorporated herein by reference. The result of the model subtraction is referred to as the residual signal. Hence, in particular a large amplitude ECG peak can be effectively reduced. As a further advantage of applying model subtraction instead of gating as a non-linear operation, a spectral content of the signal which is then provided to the subsequent signal processing steps may be less distorted.

In a subsequent step, the residual signal is provided to the filter unit comprising a notch filter. The filter unit can effectively reduce a second, periodic unwanted signal component such as power line noise at 50 or 60 Hz by applying the notch filter. Thanks to the preceding model subtraction step, it is possible to apply a very sharp notch filter. An advantage is that even a very sharp notch filter will have less impact on the overlapping desired spectrum of the EMG activity. The resulting signal is referred to as the filtered signal.

The filtered signal is then provided to a subsequent gating step. As indicated by the name, the gating unit can be seen as a gate which passes a signal at an input on to an output if the gate is open and blocks the signal if the gate is closed. In other words, the gating unit is configured to selectively pass the received filtered signal on to its output. For example, the gating unit passes the received filtered signal to its output if an amplitude or RMS (root mean square) value of the filtered signal or RMS of the model of the first unwanted signal component is below a predetermined threshold. The gating unit can comprise an input for receiving the model of the first unwanted signal component. Optionally, during periods in which the input signal is not directly passed on to its output, the gating unit may provide at its output, for example, a value of the received filtered signal immediately preceding the gating, an average of the received filtered signal or zero output. The output of the gating unit is referred to as the gated signal. For example, the gated signal can be an EMG signal from which ECG and power line contaminations have been removed. The gated signal can then be used for subsequent signal processing such as determining a neural respiratory drive (NRD) of a COPD patient.

It should further be noted that the gating step may further reduce residual ECG contaminations due to jitter and/or variability of ECG waveform from one heart-cycle to another heart-cycle which are not removed by the model subtraction unit. The proposed solution thus partly reduces the first unwanted signal component, subsequently reduces the second unwanted signal component, and then again addresses a remainder of the first unwanted signal component by gating. As a further advantage, a model subtraction of reduced complexity, i.e., which may require less computational resources, may be used because the subsequent gating step can further reduce remaining contaminations due to imperfect model subtraction of the first unwanted signal component.

It should further be noted that in conventional systems a filtering step would usually be implemented as the first step. In particular, because a filter is often already included in commercially available input amplifier stages which could thus be used by a person skilled in the art without further modification.

In an embodiment, the processing apparatus can be configured to process an electromyography (EMG) signal as the physiological signal. An EMG signal is typically a rather weak signal, in particular if parasternal respiratory muscles are being measured using surface electrodes attached to a skin of a subject. An EMG signal may particularly benefit from the proposed signal processing for removing or at least reducing unwanted signal components.

In an embodiment, the model subtraction unit is configured to reduce, as the first unwanted signal component, an electrocardiography (ECG) signal component, comprised in the physiological signal, in particular an electrocardiography signal component comprising a QRS complex. A typical shape of electrocardiography signals is known and can thus be identified in the received physiological signal such as an EMG signal. For example, the R-peak of the ECG can be identified using the Pan-Tompkins algorithm, J. Pan and W. J. Tompkins, "A real-time QRS detection algorithm", IEEE Trans. Biomed. Eng., vol. 32, no. 3, pp. 230-236, 1985. A shape of the ECG signal can be modeled around such peaks based on models of known typical ECG shapes or advantageously using the approach disclosed in WO 2015/044010 A1 of the applicant. The model subtraction unit can be configured to subtract unwanted signal components such as determined QRS complexes, R-peaks, or longer segments such as a PQRST sequence from the received physiological signal to obtain a residual signal.

In an embodiment, the filter unit can be configured to reduce, as the second unwanted signal component, a power line signal component comprised in the physiological signal. In a refinement, the notch filter is configured to attenuate a power line frequency, in particular 50 Hz or 60 Hz. An advantage of this embodiment is that the filter unit filters out the mains hum from the 50/60 Hz power line. Thereby the notch filter removes power line frequency components.

In an embodiment, the model subtraction unit is configured to determine the model of the first unwanted signal component from a plurality of cycles of the first unwanted signal component. This is particularly advantageous if the first unwanted signal component is uncorrelated with the second unwanted signal component. If the model of the first unwanted signal component is determined from a plurality of cycles of the first unwanted signal component in the received signal, averaging can thus be used to reduce an impact of the second unwanted signal component on the model of the first unwanted signal component. For example, the impact of power line noise on the ECG model can be reduced. For example 30-60 heart-cycles can be used to effectively average out the power line noise on the ECG template or model.

In an embodiment, the model of the first unwanted signal component can comprise a waveform indicative of the first unwanted signal component. For example, the first unwanted signal component can be an R-peak or QRS complex of an ECG signal and the model of the first unwanted signal component comprises the shape of a typical QRS complex as the waveform indicative of the first unwanted signal component which can thus be removed from the received physiological signal by the model subtraction unit. Further, the first unwanted signal component can comprise the P-wave and/or T-wave of an ECG signal.

In an embodiment, the model subtraction unit can comprise a peak detector. For example, a Pan-Tomkins algorithm can be used to efficiently detect R-peaks in an ECG signal. These peaks are advantageously used by the model subtraction unit to identify locations where a waveform or waveform template indicative of the first unwanted signal components such as a QRS complex of an ECG signal should be placed.

In an embodiment, the gating unit can be configured to cap or block the filtered signal if a value indicative of the filtered signal exceeds a predetermined threshold. The gating unit can thus prevent the filtered signal as an input from being directly forwarded to its output as the gated signal if the predetermined threshold is exceeded. This gating may also be based on a value indicative of the filtered signal such as an RMS value of the filtered signal.

In an embodiment, the gating unit can be configured to cap or block the filtered signal if a value indicative of the model of the first unwanted signal component exceeds a predetermined threshold. The gating unit may thus optionally receive the model of the first unwanted signal component as an input and control the gating based thereon. The gating can also be controlled based on the filtered signal and the model of the first unwanted signal component. For example, gating can be applied if a power ratio between model and the filtered signal exceeds the predetermined threshold. In the alternative or in addition, the gating unit may receive the model of the first unwanted signal at an input and control the gating based on a value indicative of the model of the first unwanted signal component. An advantage of this embodiment is that information about the first unwanted signal component as provided by the model subtraction unit can be used to control the gating such that residual influences from the first unwanted signal component such as an ECG signal component can be further reduced by the gating unit. It is to be understood that the filtered signal, for example an amplitude of the filtered signal, or the model of the first unwanted signal component can be directly considered. In addition or in the alternative, a value indicative of at least one of these signals can be determined for example an RMS (root mean square) value can advantageously be considered to control the gating.

In a refinement of this embodiment, the threshold can be an adaptive threshold, in particular adaptive based on a median root mean square (RMS) value of the model of the first unwanted signal component. An advantage of this embodiment is that in long term measurements, the threshold can be adapted to changing measurement conditions.

In a further refinement, the threshold can be an adaptive threshold based on a quality criterion indicative of a match between at least a part of the model of the first unwanted signal component and the physiological signal. For example, the gating unit can be controlled on how well the model matches with regard to a P-wave, QRS-wave and/or T-wave of an ECG contamination in the received physiological signal. Hence, different parts of the model can have different thresholds for gating the received filtered signal, for example, for gating different parts of the ECG contamination.

In an embodiment, the gating unit can be configured to apply a binary mask of gate-regions to the filtered signal to further reduce the first unwanted signal component. A gate-region refers to a signal portion, wherein the gating unit does not directly pass the received filtered signal to its output as the gated signal. The binary mask can be determined by the model subtraction unit and provided to a gating signal to the gating unit. The binary mask may be determined based on an RMS value of the model of the first unwanted signal component.

In a refinement, the gating unit can be configured to reconstruct the filtered signal in a gate-region, in particular based on a signal level of the filtered signal before and/or after the gate-region. An advantage of this embodiment is that the gated signal provided as an output of the gating unit does not provide for example zero values as its output during the gating where the signal is capped but can provide for example the last value preceding the gate-region or alternatively the first value after the gate-region for non-real-time applications. It is to be understood that other types of reconstruction can be applied such as interpolation.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
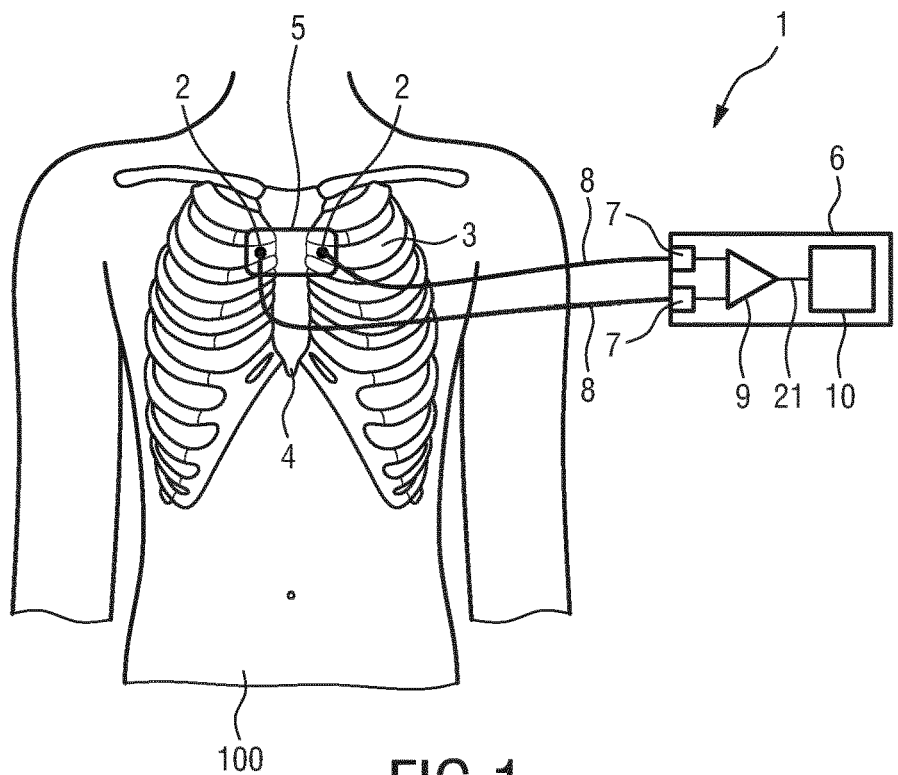
FIG. 1 shows a simplified schematic of an electromyography system applied to a subject.

FIG. 1 shows an embodiment of an electromyography system 1 comprising a processing apparatus 10 for processing a physiological signal using model subtraction, notch filtering and gating. The processing apparatus 10 will be described in more detail with reference to FIG. 3.

The electromyography system 1 shown in FIG. 1 further comprises two electrodes 2 for application to a skin of a subject 100. For assessment of an inspiratory respiratory-effort, an electromyography (EMG) signal can be measured via the two EMG surface electrodes 2 located at a second intercostal space 3 symmetrically with respect to the sternum 4 of the subject 100, i.e., as a parasternal measurement. The subject can be a patient suffering from chronic obstructive pulmonary disease (COPD). The two EMG electrodes 2 can be disposable electrodes which can be clicked electrically onto an EMG patch 5 or wearable device that is worn for a single or a multiple days at the general ward of the hospital or the home. For example, the two electrodes can be mounted inside or attached on a single EMG patch 5, which eases the placement of the electrodes and helps to assess the same respiratory muscle groups for subsequent measurement.

At the given location on the body of the subject 100, the electrodes 2 mainly measure an inspiratory breathing effort due to the activation of the parasternal intercostal muscles during inhalation. This can serve as a powerful indicator for the detection of exacerbation for COPD patients in the hospital or the home. An amount of respiratory effort due to quiet breathing can be determined from the voltage that is measured across the two EMG electrodes 2. A maximum power of the EMG measured at the second intercostal parasternal muscle during inhalation can be determined and used as an indicator of day-to-day deterioration or improvement of a COPD patient when multiple measurements are performed over a number of days. This can also serve as a predictor of hospital readmission after discharge. A differential measurement can be performed to reliably measure weak signals. The EMG signals to be measured typically have an amplitude in the range of 3 to 50 uV. For reliable signal analysis, any contaminant signal components such as ECG contaminations and power line noise should be removed.

The electromyography system 1 in this embodiment comprises a base unit 6 which in turn comprises the processing apparatus 10 for processing the electromyography signal. The base unit 6 comprises an interface 7 which is electrically connected to the electrodes 2 via signal leads 8. The input ports of the interface 7 are connected to a differential amplifier 9 which provides the EMG signal 21 as the physiological signal as an input to the proposed processing apparatus 10.

It should be highlighted that the measured EMG signal 21 received by the processing apparatus 10 may also comprise contaminations from other sources such as power line noise and unwanted ECG signal components.

The problem of power line noise, i.e., 50 or 60 Hz sinusoidal noise, can occur in measurement equipment where there is an impedance mismatch between the electrodes 2 and/or the cables 8. As explained above, such a mismatch can be due to poor shielding of the cables 8 and/or poorly mounted electrodes 2. The first can occur when cost-effective equipment is used and a second can occur for example when the person applying the EMG electrodes 2 is less experienced. Both situations can easily arise in a home situation where for example a COPD patient at home needs to measure an inspiratory EMG activity. Usually, home equipment should be low-cost. Moreover, the patient himself and/or a health-coach needs to take care of the application of the EMG electrodes 2. Hence, the electrodes 2 may be applied imperfectly by a layperson instead of highly qualified medical personnel.

Figure 2:
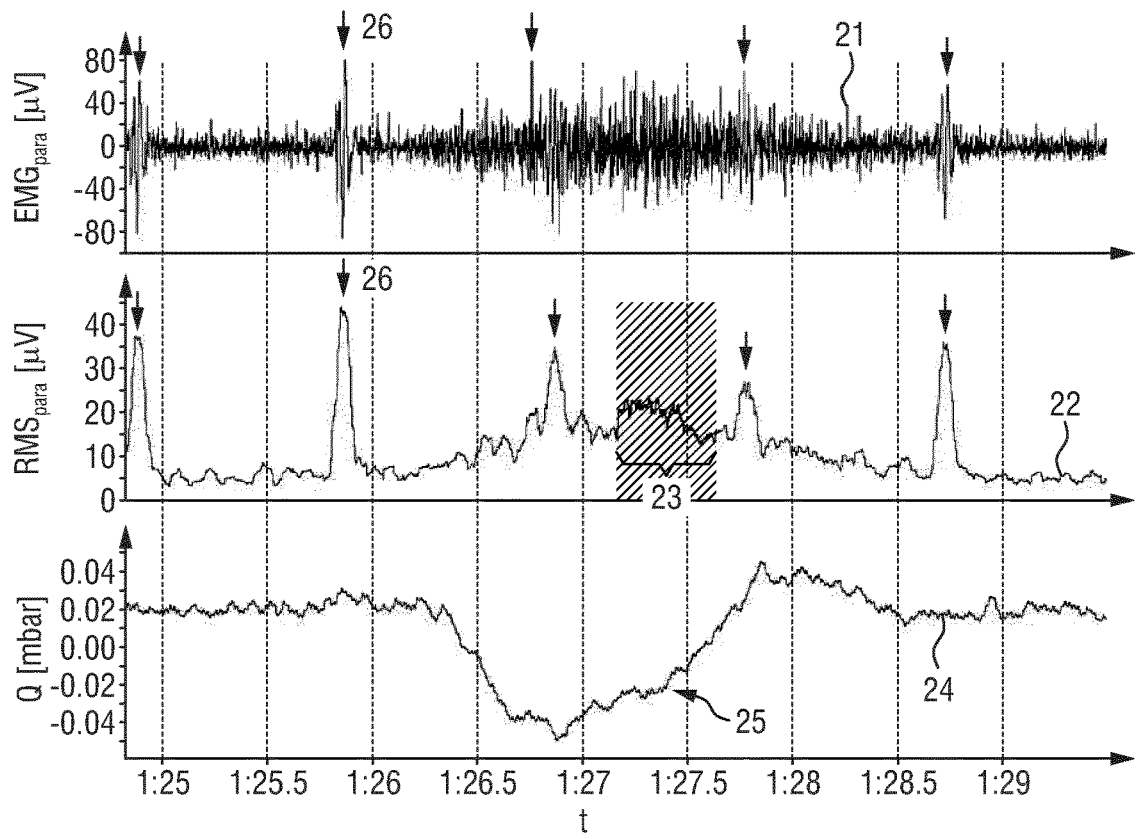
FIG. 2 shows exemplary graphs of a respiration measurement using electromyography.

FIG. 2 shows an exemplary graph of a respiration measurement. The top graph shows of an EMG signal 21 as the received physiological signal comprising a first and a second unwanted signal component. The horizontal axis in the graphs as shown in FIG. 2 denotes the time t. In the top graph, the vertical axis denotes an amplitude $EMG_{para}$ of a parasternal EMG measurement. The middle graph in FIG. 2 shows an RMS (root mean square) value 22 of the EMG signal 21 as shown in the upper graph in FIG. 2. In the middle graph, the vertical axis denotes an RMS amplitude $RMS_{para}$. The highlighted part 23 in the middle graph indicates a maximum RMS segment which can be used for clinical assessment of the patient 100 as a measure indicative of the parasternal muscle activity during inspiration.

The lower graph in FIG. 2 shows a pressure curve 24 as measured by a nasal cannula. The vertical axis denotes the pressure Q measured in the nose of the patient. The valley 25 in this graph indicates a phase of inspiration. The parasternal muscle activity 23 during the inspiration phase 25 indicates that the patient activates the parasternal muscles to actively support breathing.

As shown in FIG. 2, a raw, measured EMG signal 21 is heavily influenced by an ECG signal contamination. ECG peaks are indicated by arrows 26. These unwanted ECG signal components can also be clearly seen in the RMS signal trace shown in the middle graph of FIG. 2. Since the EMG signal 21 is measured at the second intercostal space, i.e., close to the heart, the ECG contaminations can have a significantly higher amplitude than the desired EMG contribution from the parasternal muscles. It would thus be advantageous to reduce contributions from unwanted signal components in the measured EMG signal 21, in particular to reduce power line noise and contaminant electrocardiogram (ECG) signals.

Figure 3:
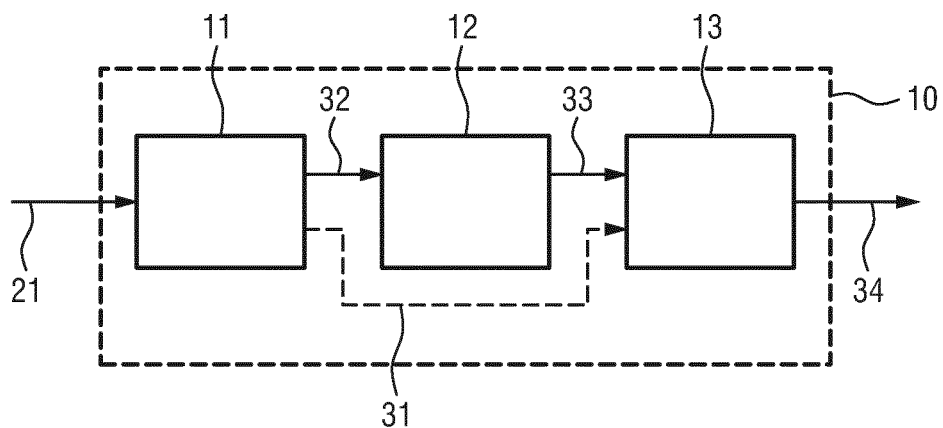
FIG. 3 shows a first schematic diagram of a processing apparatus according to an aspect of the present disclosure.

FIG. 3 shows an embodiment of a processing apparatus 10 for processing a physiological signal 21 using model subtraction, notch filtering and gating. The processing apparatus 10 comprises a model subtraction unit 11 configured to receive the physiological signal 21 and to reduce a first unwanted signal component in the physiological signal 21 by subtracting from the physiological signal a model 31 of the first unwanted signal component to obtain a residual signal 32. The filter unit 12 is configured to receive the residual signal 32 and to reduce a second unwanted signal component in the residual signal 32 by applying a notch filter to obtain a filtered signal 33. The gating unit 13 is configured to receive the filtered signal 33 and to apply gating to the filtered signal 33 to obtain a gated signal 34 which can then be provided at an output of the processing apparatus 10 for further processing. Optionally, the model 31 of the first unwanted signal component can also be provided from the model subtraction unit 11 to the gating unit 13 to control the gating of the filtered signal based thereon. Exemplary embodiments of the respective components and the signal processing flow will be described with reference to the following drawings.

Figure 4:
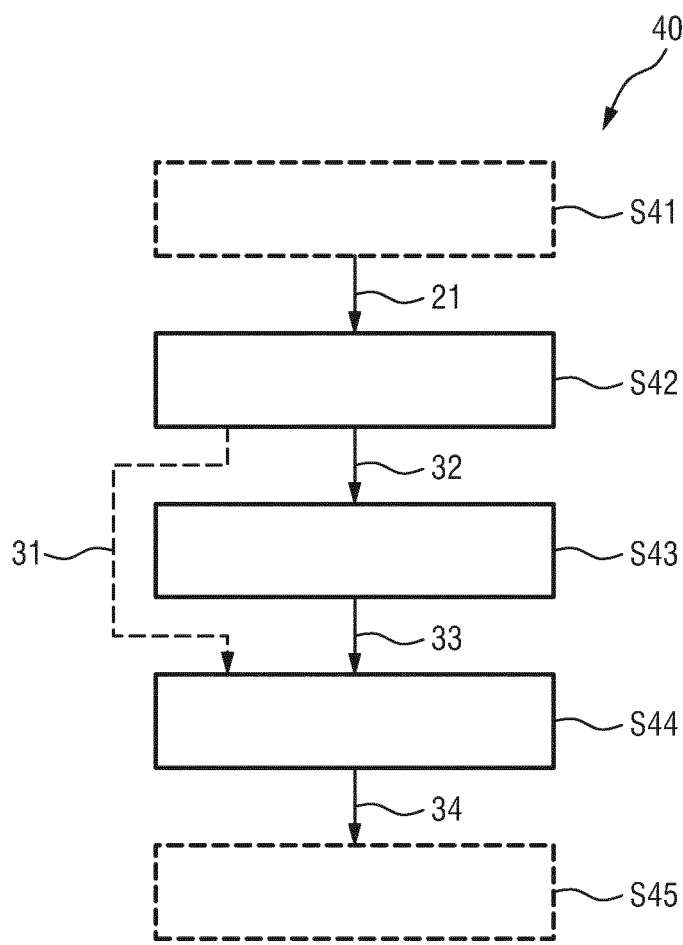
FIG. 4 shows a flow chart of a method for processing a physiological signal according to an aspect of the present invention.

FIG. 4 shows an exemplary flow chart of a method 40 for processing a physiological signal 21 using model subtraction, notch filtering and gating. The method as shown in FIG. 4 also shows the preceding step S41 of acquisition of an EMG signal 21 as the physiological signal. It should be noted that the EMG signal 21 can either be directly acquired, for example using an electromyography system S1 as shown in FIG. 1, or that the EMG signal can also be obtained (i.e., received or retrieved), for example from a database or storage source, and can be processed as described by the following method steps at a later point in time and/or at a remote location for example in form of a cloud based service.

In step S42 the physiological signal, here the EMG signal 21, comprising the first and second unwanted signal components is received and the first unwanted signal component in the physiological signal is reduced by subtracting from the physiological signal a model 31 of the first unwanted signal component to obtain a residual signal 32.

In a subsequent step S43, the second unwanted signal component in the received residual signal 32 is reduced by applying a notch filter to obtain a filtered signal 33.

In a subsequent step S44, gating is applied to the received filtered signal 33 to obtain a gated signal 34.

In a subsequent step S45, the received gated signal 34 can be processed further. For example a signal power of the gated EMG signal can be evaluated to determine information about the neural respiratory drive (NRD) as a powerful indicator of the condition of a COPD patient.

Optionally, the model 31 of the first unwanted signal component as determined in step S42 can be provided as an input to the gating step S44 to control the gating of the filtered signal based on the model 31 of the first unwanted signal component. An advantage of this embodiment is that the first unwanted signal component which has already been reduced by the model subtraction step S42 can be further reduced in the gating step S44. This is particularly advantageous in case of a mismatch between the first unwanted signal component and the model 31 of the first unwanted signal component. Such a mismatch can occur if the amount of cancellation obtained by the model subtraction step S42 is not sufficient, for example, in case of jitter or heart beat to heart beat fluctuations or mismatch between an assumed ECG shape of the model and the actual shape of the ECG pulse contaminating the EMG signal 21.

Further, alternatively or in addition, the gating by the gating unit can be controlled based on a quality criterion indicative of a match between at least a part of the model of the first unwanted signal component and the physiological signal, for example, on how well the model matches with regard to a P-wave, QRS-wave and/or T-wave of an ECG contamination in the received physiological signal. If the model matches sufficiently well with the unwanted signal component, for example, in the absence of jitter or heart beat to heart beat fluctuations, the model identification and model subtraction can already lead to a sufficient reduction of the first unwanted signal component. The gating unit can thus be configured to pass the filtered signal 33 on to its output without gating or blocking, if the quality criterion indicates a match.

Figure 5A:
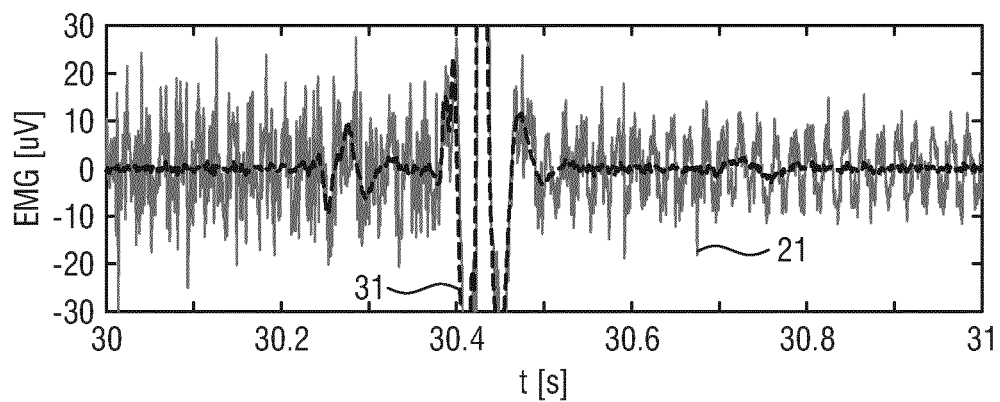
FIG. 5A to 5C show a first set of exemplary signals.
Figure 5B:
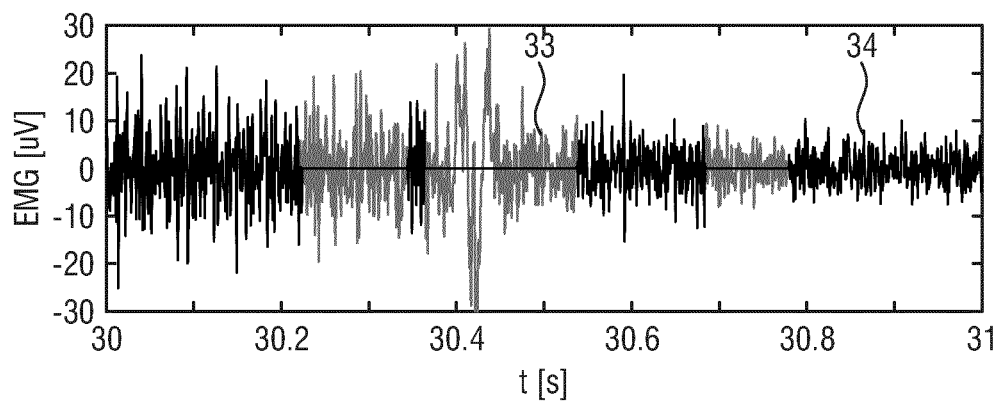
Figure 5C:
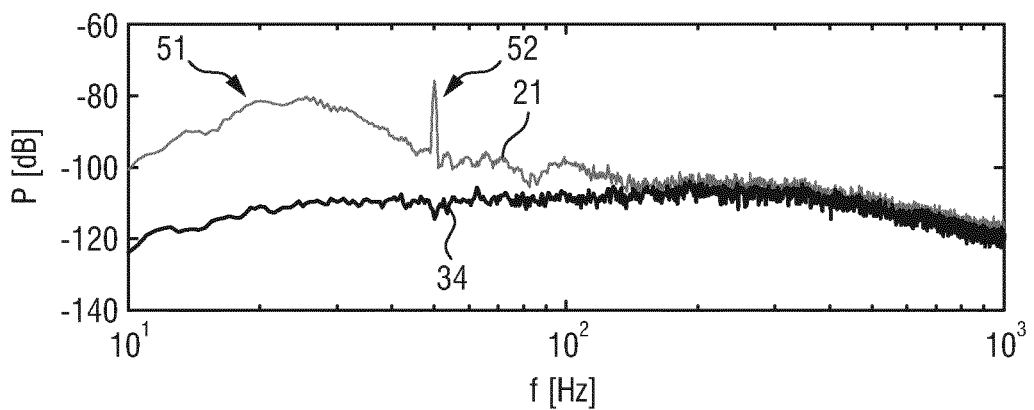

FIG. 5A to 5C show a first set of exemplary signals at different stages of the proposed signal processing. In FIGS. 5A and 5B the horizontal axis denotes the time tin seconds, whereas the vertical axis denotes an amplitude of the respective physiological signal 21, model 31, filtered signal 33 and gated signal 34. The received physiological signal 21 and the model 31 are shown in FIG. 5A. The filtered signal 33 and the gated signal 34 are shown in FIG. 5B. FIG. 5C shows a power spectrum of the received physiological signal 21 and of the gated signal 34. The horizontal axis denotes the frequency fin Hz and the vertical axis denotes the power in dB.

The received signal 21 can be substantially contaminated, in particular, as the first unwanted signal component, by an ECG signal component and, as the second unwanted signal component, a power line signal component. The unwanted ECG signal component can provide a strong contribution in the lower frequency range as indicated by reference numeral 51 in FIG. 5C. The periodic power line signal component can be clearly seen as a strong peak in the power spectrum at 50 Hz as indicated by reference numeral 52 in FIG. 5C.

The model subtraction unit 11 receives the EMG signal 21 and determines a model 31 of the first unwanted signal component, here of the unwanted ECG signal component, as shown in FIG. 5A. The model subtraction unit 11 then subtracts from the physiological signal 21 the model 31 of the first unwanted signal component to obtain the residual signal 32.

In a next step, the filter unit 12 receives the residual signal 32 and reduces the unwanted power line signal component in the residual signal 32 by applying a notch filter, here a notch filter at 50 Hz, to obtain the filtered signal 33 as shown in FIG. 5B.

In a next step, the gating unit 13 receives the filtered signal 33 and applies gating to the filtered signal to obtain a gated signal 34 as illustrated in FIG. 5B. An exemplary gating will be described in more detail with reference to FIGS. 10 and 11. In the shown embodiment, those parts of the filtered signal as received by the gating unit 13 are capped, i.e., removed, where an amplitude of the model 31 of the first unwanted signal component or an RMS value of the model 31 exceeds a predetermined threshold and only those parts wherein the ECG model shows a contribution below said threshold are passed on to an output of the gating unit 13 and are provided as the gated signal 34 for further processing.

It should be noted that the ECG model 31 not only shows the QRS complex at around 30.4 seconds, but also the P wave at around 30.3 seconds and the T wave at around 30.7 seconds. As can be seen from the gated signal 34 in FIG. 5B, all these QRS, P and T components are properly gated by the gating unit. In other words, the contamination due to the ECG signal can be successfully reduced while at the same time ensuring that a large amount of the useful EMG signal is passed onto the output of the signal processing apparatus.

Figure 6A:
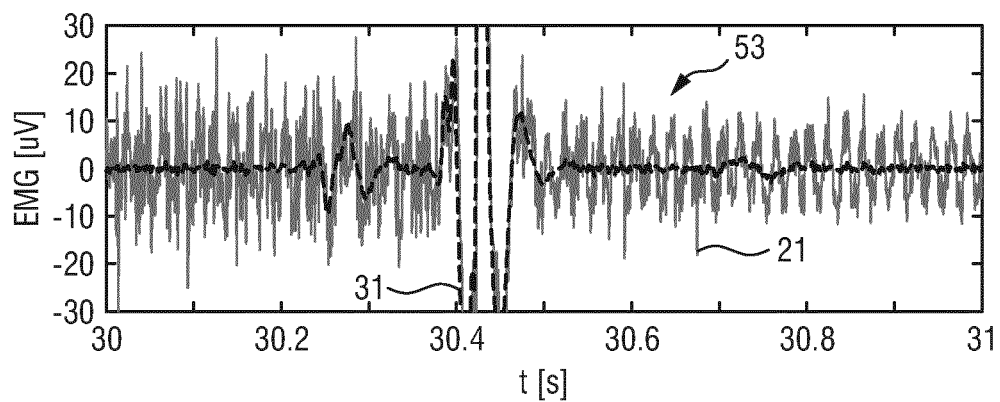
FIG. 6A to 6C show a second set of exemplary signals for a modified processing apparatus.
Figure 6B:
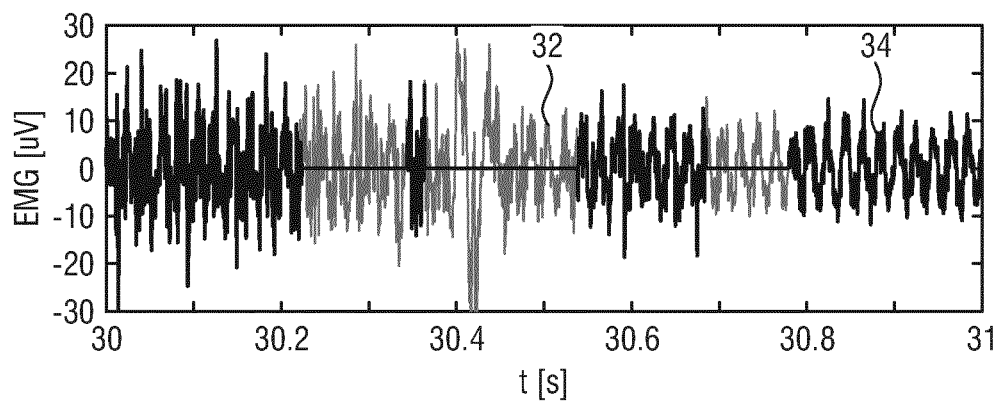
Figure 6C:
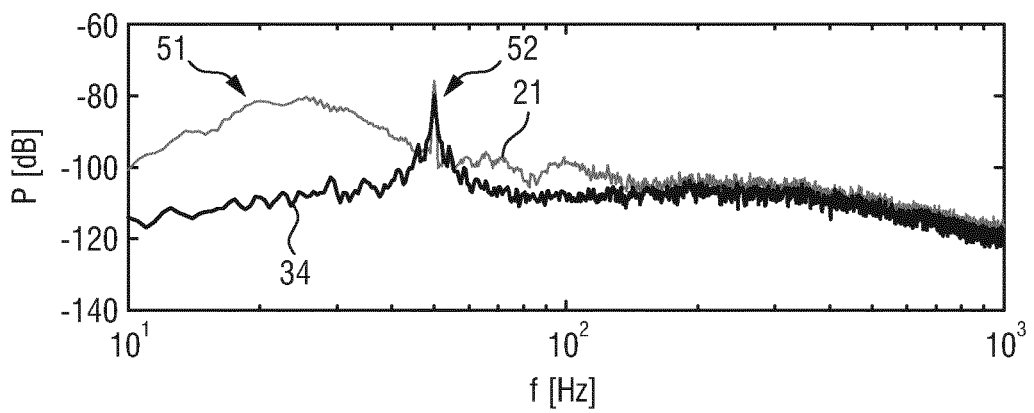

For comparison, FIG. 6A to FIG. 6C illustrate a modification of the scenario as shown in FIG. 5A to 5C. without applying a filter unit 12 comprising a notch filter between the model subtraction unit 11 and the gating unit 13 of FIG. 3. In other words, the filter unit 12 is removed. If no notch filter is applied between the model subtraction unit 11 and the gating unit 13, the gated signal 34 as the output of the processing apparatus 10 experiences significant distortion around the power line frequency 50 Hz, as indicated by reference numeral 52 in FIG. 6C. The 50 Hz oscillation is also clearly visible in the time-domain in FIG. 6A, as indicated by reference numeral 53. The residual signal 32 as the output of the model subtraction unit 11 is shown in FIG. 6B.

Power line noise can be effectively reduced from a measured physiological signal 21 by applying a notch filter. For the case of EMG signal there can be a spectral overlap between the desired EMG signal and power line noise in the 50 Hz and/or 60 Hz regions. It would thus be desirable to keep the notch filter as sharp as possible. For example in case of 50 Hz power line noise a notch filter can be provided that has −3 dB points stretching from 49 Hz up to 51 Hz. However, such a sharp notch filter can give rise to so-called ringing artifacts due to the large group-delay of the filter. In the situation of the notch filter from 49 Hz up to 51 Hz, ringing artifacts can be experienced that are larger than −40 dB for a duration of a few tens of seconds after applying a delta Dirac test signal as an input to the notch filter. Since an ECG contamination can sometimes be 40 dB or more higher compared to an inspiratory EMG activity for frequencies for example from 10 up to 60 Hz, these ringing artifacts can cause a significant disturbance signal on the EMG signal.

Figure 7A:
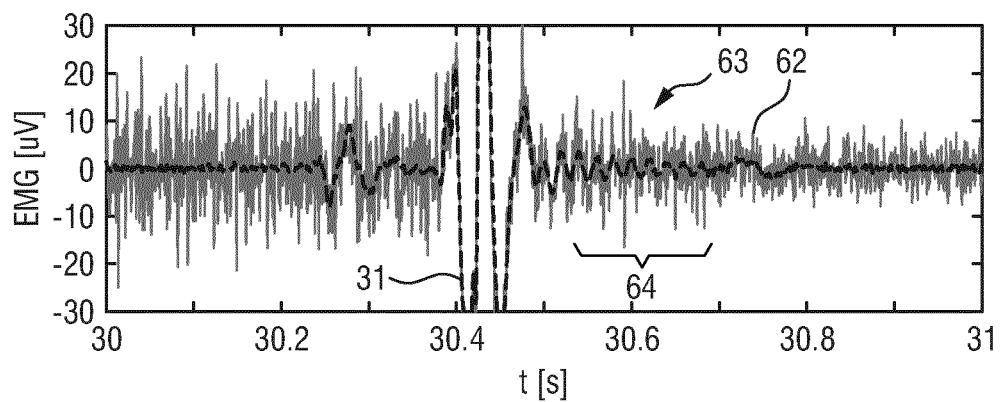
FIG. 7A to 7C show a third set of exemplary signals for a modified processing apparatus.
Figure 7B:
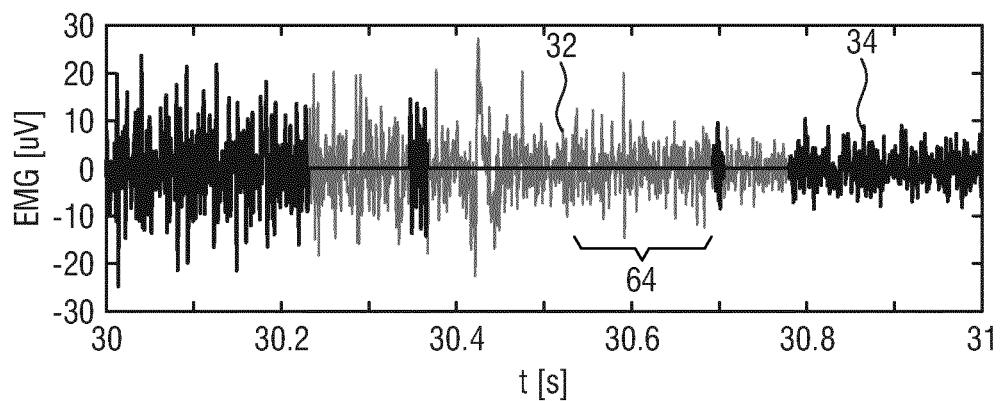

To illustrate the advantages of the proposed arrangement of FIG. 3, a modification of the arrangement will be described with reference to FIG. 7A to 7C. In FIG. 3, the filter unit 12 is arranged in between the model subtraction unit 11 and the gating unit 13. In the modified arrangement, the filter unit 12 comprising the notch filter is arranged as the first processing step which is then followed by the model subtraction unit 11 and the gating unit 13 as subsequent steps. The graphs for the proposed arrangement of FIG. 3 are shown in FIG. 5A to 5C. The graphs for the modified arrangement are shown in FIG. 7A to 7C.

Figure 7C:
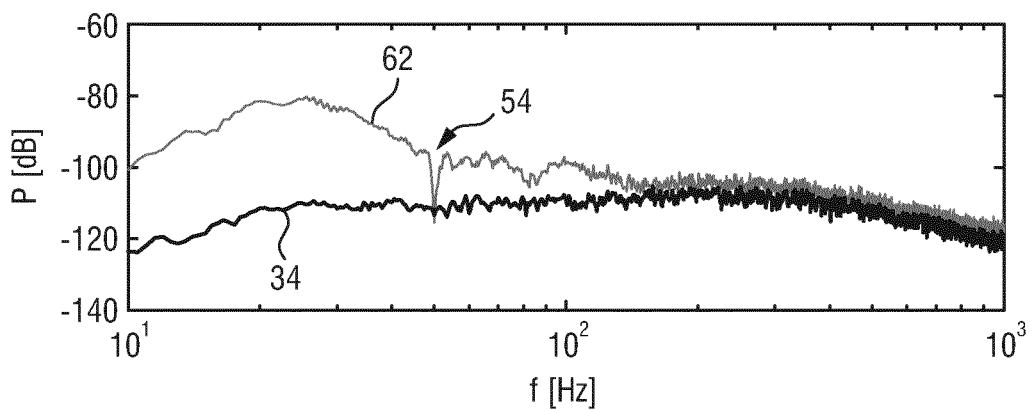

In FIG. 7C, signal trace 62 illustrates the output of the notch filter having a sharp notch 54 at 50 Hz. The output signal 62 of the notch filter is provided as an input to the subsequent model subtraction and gating steps. As can be seen in FIG. 7A, the notch filter introduces significant ringing artifacts 63, in particular in a period 64 immediately following the main peak of the model 31 of the unwanted ECG component. Applying the notch filter before the model subtraction can thus result in additional harmonics in the model signal. Provided that the gating unit controls the gating based on such a disturbed model 31, these additional harmonics can subsequently result in additional capping of the signal in the gating step, because the additional harmonics represent energy and the gating unit may be configured to cap signal components when the model 31 signal or its RMS value exceeds a predetermined threshold. In consequence, the EMG signal during section 64 may be disregarded and not forwarded to the output by the gating unit 13. This can thus result in significant loss of remaining EMG signal in the gated signal 34. The gated signal 34 is illustrated by the bold line in FIGS. 5B and 7B, where it can be seen that section 64 is disregarded and not forwarded to the output. It will be appreciated that there are also other scenarios possible for the gating, for example, by using a combination of the model 31, residual signal 32 and/or output signal 62 of the notch filter. In such cases, the ringing artifacts of the notch filter may again be included in the model and again can lead to a reduction of the desired EMG energy in the output after gating. The signal loss can also be seen by direct comparison of FIG. 5C and FIG. 7C. The power level of the gated signal 34 with the modified arrangement in FIG. 7C, wherein the notch filter is used as the first stage, is slightly lower than the power level of the gated signal 34 in FIG. 5C as obtained with the proposed processing apparatus 10 as shown in FIG. 3.

An exemplary model subtraction is described in the following with reference to FIG. 8 and FIG. 9.

Figure 8:
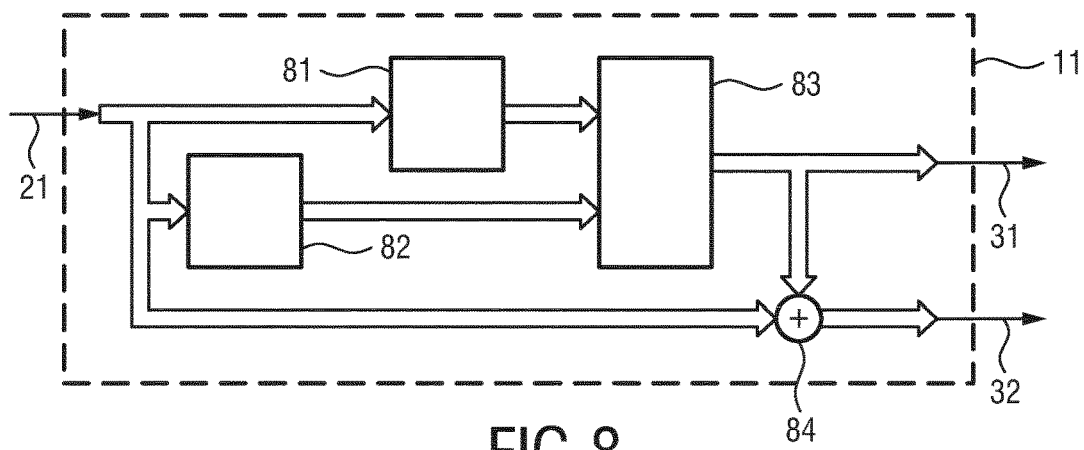
FIG. 8 shows an exemplary embodiment of a model subtraction unit.

FIG. 8 shows an exemplary embodiment of a model subtraction unit 11 in more detail. The physiological signal, here the measured EMG signal 21 measured at the second intercostal space parasternal muscles, is heavily contaminated by an ECG component. The ECG signal usually has a higher energy than the EMG signal itself. In order to accurately estimate an index of neural respiratory drive (NRD) from the EMG signal, the ECG contamination in the EMG measurement, as a first unwanted signal component, has to be removed. FIG. 9 comprises a top graph, an upper middle graph, a lower middle graph, and a bottom graph. The top graph in FIG. 9 shows an example of a measured EMG signal 21 wherein the R-peaks of the unwanted ECG component are clearly visible. These R-peaks are marked by crosses and some exemplary peaks 26 are indicated by arrows in all graphs of FIG. 9. Furthermore, as can be seen from curve 32 in a lower middle graph and curve 35 in the bottom graph of FIG. 9, four waves of intercostal muscle activity can be seen.

Figure 9:
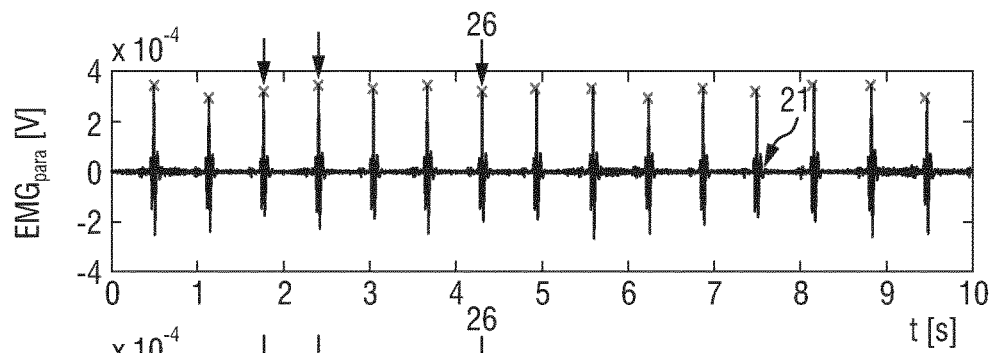
FIG. 9 shows exemplary corresponding signal traces.
Figure 9:
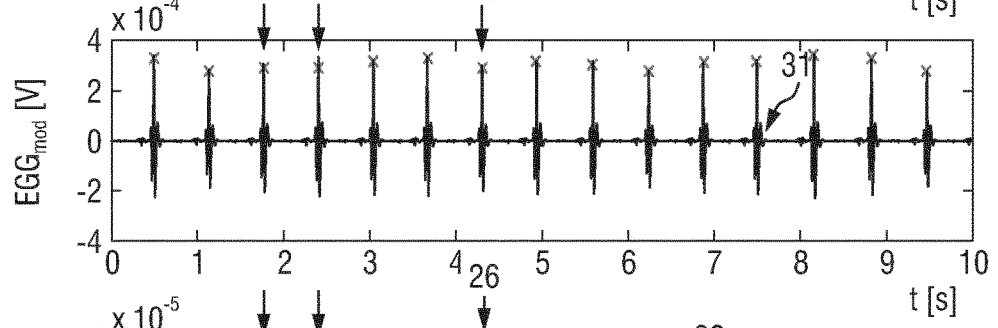
Figure 9:
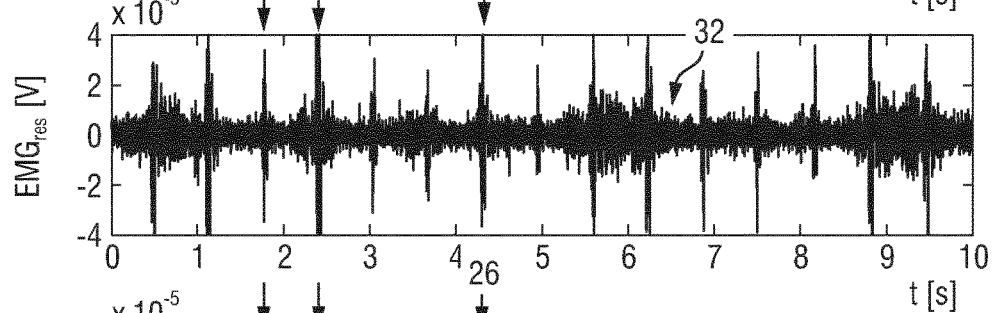
Figure 9:
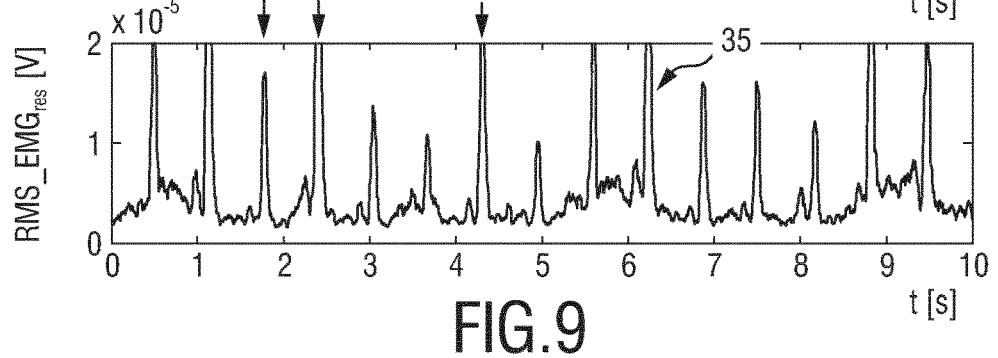

Referring again to FIG. 8, the EMG signal 21 as exemplary shown in the upper graph of FIG. 9 is received as an input of the model subtraction unit 11. In a first step 81 peak detection is applied, for example, using the Pan-Tomkins algorithm to robustly detect the R-peaks in the QRS complexes of the ECG contamination. After detecting the R-peaks, as indicated by the crosses in the upper graph in FIG. 9, a model of the ECG shape can be obtained for each single cardiac cycle as for example explained in WO 2015/044010 A1. An exemplary ECG model $ECG_{mod}$ 31 is shown in the upper middle graph of FIG. 9. As can be seen, EMG activity related to breathing is not present in the shown ECG model. For further details of the technique used for obtaining the ECG model, reference is made to WO 2010/044010 A1. Optionally, a low pass filter 82 can be applied before the actual ECG modeling step 83.

The ECG model 31, as an estimation of the ECG signal superimposed on the desired EMG signal, is then subtracted in step 84 from the raw received EMG signal 21 to reduce the ECG contamination.

It should be noted that, using the approach proposed herein, it is also possible to apply an ECG model of limited accuracy which does not perfectly remove the ECG signal from the EMG signal 21. For example some variability in the ECG shape in successive cardiac cycles or jitter may still be present. This can also be seen in the lower middle and bottom graphs in FIG. 9, wherein some residual influence due to the ECG contamination is visible in the residual signal $EMG_{res}$ 32 as exemplarily indicated by the arrows. This remaining ECG contamination is more clearly visible in an RMS computation, which exemplarily computes the average of the residual signal 32 with a window of 50 ms. The root mean square $RMS\_EMG_{res}$ 35 of the residual signal $EMG_{res}$ 32 is indicated in the bottom graph of FIG. 9.

In a next step, the residual signal $EMG_{res}$ 32 is provided to the filter unit 12 as shown in FIG. 3, to reduce a second unwanted signal component in the residual signal 32, here to reduce power line noise at 50 Hz, by applying a notch filter centered at 50 Hz to obtain filtered signal 33. The filtered signal 33 is then provided as an input to the gating unit 13.

An exemplary gating unit 13 is described in more detail with reference to FIGS. 10 and 11. FIG. 11 comprises a top graph, an upper middle graph, a lower middle graph, and a bottom graph illustrating signal traces at different stages of the signal processing.

The gating unit 13 receives the filtered signal 33, i.e., the output of the filter unit 12 as an input. In an advantageous embodiment as shown in FIG. 3 and FIG. 10, the gating unit 13 can further receive the model signal or model 31 of the first unwanted signal component as a second, optional input.

The gating unit 13 can further reduce a residual ECG contamination in the filtered signal 33, which has already undergone the preceding steps of model subtraction by the model subtraction unit 11 and notch filtering by the filter unit 12. The gating unit 13 can apply a binary mask to the filtered signal 33. The gating can advantageously be controlled based on the model 31 of the first unwanted signal component.

Figure 10:
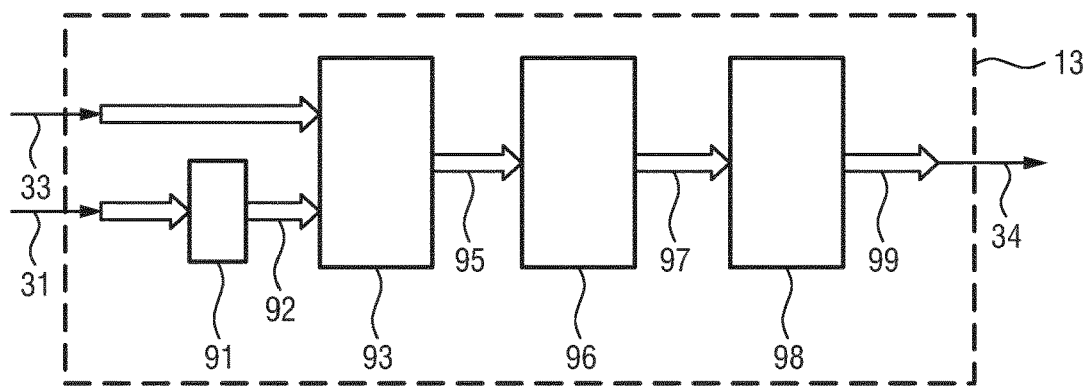
FIG. 10 shows an exemplary embodiment of a gating unit.
Figure 11:
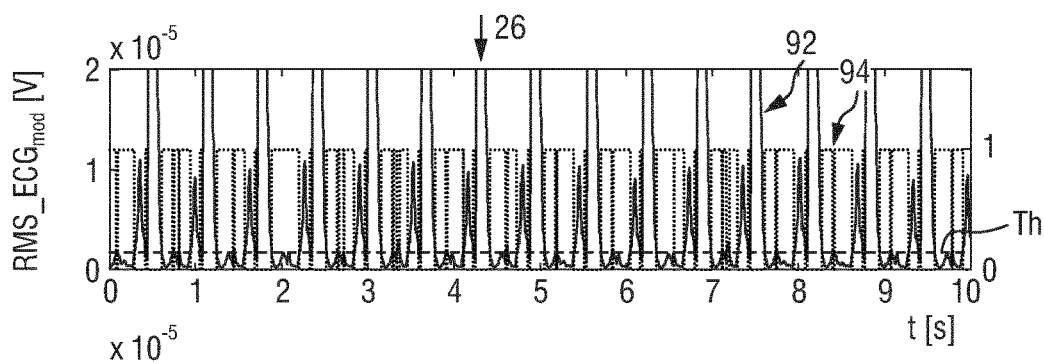
FIG. 11 shows exemplary graphs of corresponding signals.
Figure 11:
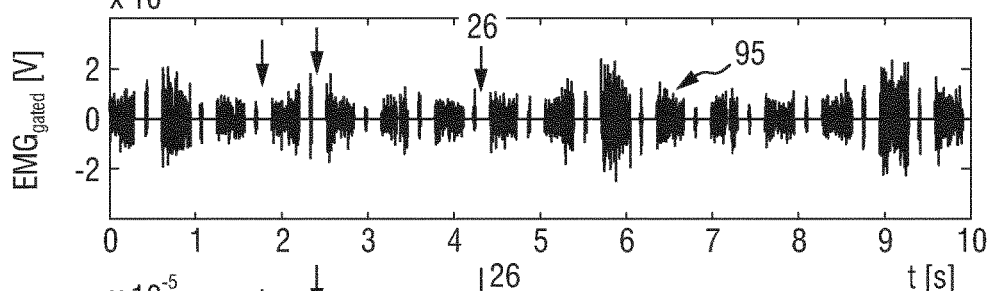
Figure 11:
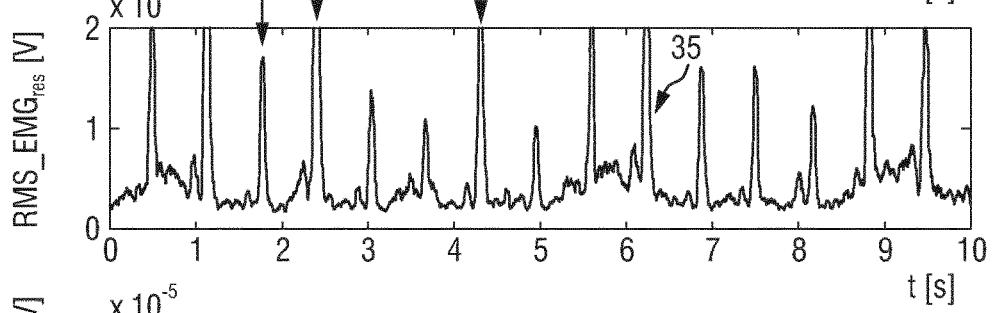
Figure 11:
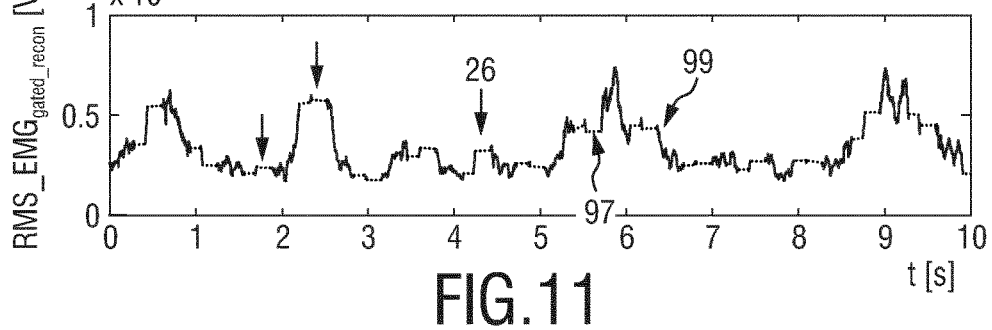

In the example shown in FIG. 10, the gating unit 13 receives the model 31 of the ECG signal component. In an optional first step 91, a root mean square $RMS\_ECG_{mod}$ 92 of the model of the ECG signal component $ECG_{mod}$ is computed as $$RMS\_ECG_{mod}(k)=\sqrt{avg[ECG_{mod}(k)]},$$

where the operator avg[ ] computes a moving average, for example a moving average of 50 ms, and the operator sqrt[ ] computes the square-root. The signal $RMS\_ECG_{mod}$ 92 is shown in the top graph FIG. 11. It should be noted that this pre-processing step can also be performed at a different stage, for example, by the model subtraction unit 11 already.

In a next step 93 the actual gating can be applied to the received filtered signal 33. For example, the filtered signal 33 can be multiplied by a binary gating signal gate(k) 94. Thereby, the input filtered signal is provided to the output if the gating signal gate(k) is true (binary 1) whereas the filtered signal is blocked if the gating signal gate(k) is false (binary 0). In the shown example, the binary gating signal 94 indicates that the RMS of the ECG model as the value indicative of the model of the first unwanted signal component, exceeds a predetermined threshold Th. The threshold Th and the binary signal 94 are exemplarily shown in the upper graph in FIG. 11. It should be noted that also an inverse logic can be applied. The binary gating signal 94 can be computed as:

$$gate(k)=RMS\_ECG_{mod}(k)<[median(RMS\_ECG_{mod})*gate\_th],$$

where k is a sample index, $RMS\_ECG_{mod}(k)$ is the RMS 92 of the modeled ECG signal component 31 and median $(RMS\_ECG_{mod})$ is a median RMS value of the modeled ECG signal component 31 within a given window, for example, a sliding window of one minute length. Furthermore, an optional parameter gate_th can be used to fine-tune the sensitivity of the gating. The value of median (RMS_ECG$_{mod}$)*gate_th is shown as the threshold Th in the top graph of FIG. 11.

This threshold Th can also be adaptive, in particular time-dependent, depending on the correctness of the model signal 31. In other words, the gating can optionally be controlled based on a quality criterion indicative of a match between at least a part of the model 31 of the first unwanted signal component and the physiological signal 21. The correctness of the model signal 31 will be typically less when there is, for example, jitter either of the P wave, QRS wave and/or T wave. Optionally, different thresholds can be applied for different segments of the model signal, here for different segments in the ECG waveform. For example, no gating is applied if the P wave can be modeled with high quality, i.e., little mismatch between model and actual ECG contamination, whereas the filtered signal 33 may still be blocked during a high-amplitude QRS complex suffering from jitter.

An averaging time or time window for RMS computation can be the same or different for the different RMS computations. For example, a first time window can be set for RMS computation of the model RMS_ECG$_{mod}$ 92 for the computation of the binary gating signal 94 gate(k), as shown in the top graph of FIG. 11. A second time window may be set for RMS computation of the RMS_EMG$_{res}$ 35 and/or RMS_EMG$_{gated\_recon}$ 99, as shown in the bottom graphs of FIG. 11. In the shown example, the time window for the ECG model is set to 25 ms, whereas the time window for the EMG signals is set to 50 ms. Setting a short time window for the model has the benefit that the gating can more quickly adjust, for example, in between the P, QRS and T regions.

In step 93, this binary gating can be applied to the received filtered signal EMG$_{filtered}$ 33 to obtain a gated EMG signal EMG$_{gated}$ 95 as the output. The gated EMG signal 95 can be computed with the binary gating signal 94 and the received filtered signal 33 as the input as follows:

$$\text{EMG}_{gated}(k) = \text{EMG}_{filtered}(k) * \text{gate}(k).$$

In an optional further step 96, after the gating step 93, an EMG signal can be reconstructed in the gate-regions to obtain a continuous reconstructed gated EMG signal from which ECG signal contaminations have been removed. A gate-region can thus refer to a region wherein the input signal is blocked by the gating, i.e., not forwarded to the output. In the shown example, the reconstruction is based on a signal level just before gating occurs. However, any other type of interpolation may be applied. The signal reconstruction may thus fill the gaps in the gated EMG signal EMG$_{gated}$ 95 in the upper middle graph in FIG. 11.

In an optional further step 98, an RMS value of the gated EMG signal 95 or the reconstructed gated EMG signal may be calculated and provided as an output 99. The RMS of the gated and reconstructed EMG signal can be provided as the gated signal 34 at an output of the gating unit 13 as shown in FIG. 10.

In an alternative embodiment, the sequence of the reconstruction step 96 and of the RMS calculation step 98 can be changed. Hence, an RMS value of the gated signal EMG$_{gated}$ 95 is calculated first and then the RMS signal is reconstructed during the gating regions. The gating regions, also indicated by signal 94, in the top graph of FIG. 11 are shown by the horizontal signal portions 97 of the reconstructed gated EMG signal EMG$_{gated\_recon}$ in the bottom graph in FIG. 11.

For comparison, FIG. 11 shows an RMS value RMS_EMG$_{res}$ of the residual signal 32, in the lower middle graph of FIG. 11 and an RMS value RMS_EMG$_{gated\_recon}$ 99 in the bottom graph of FIG. 11. The two lower graphs of FIG. 11 thus illustrate the difference between the RMS of the intermediate EMG signal which still suffers from ECG contaminations as indicated by the arrows 26 and the RMS of the ECG-removed, gated and reconstructed EMG signal using the gating technique described above.

It should be noted that the implementation of the gating technique as described herein with reference to FIGS. 10 and 11 is an exemplary gating which can be performed by using the identified ECG model 31 of the ECG contamination as the first unwanted signal component. By means of the median operator in the ECG model, the thresholds to compute the boundaries of the gate can be adaptively determined.

Figure 12:
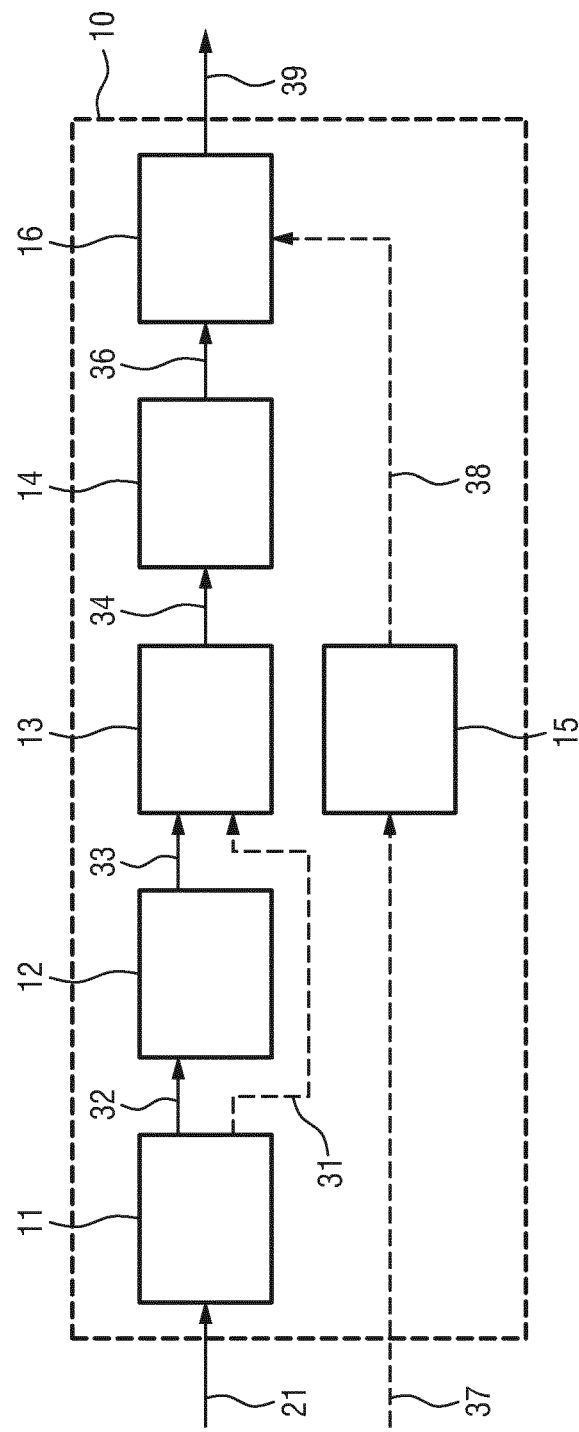
FIG. 12 shows a second schematic diagram of a processing apparatus according to an aspect of the present disclosure.

FIG. 12 shows a second embodiment of a processing apparatus 10 for processing a physiological signal 21 using model subtraction, notch filtering and gating. The processing apparatus 10 as shown in FIG. 12 comprises the components as described with reference to FIG. 3. Moreover, in an optional power computation unit 14 an RMS power of the signal can be determined and provided as an output 36. For the case of evaluating a parasternal intercostal muscle activity, the RMS power can be indicative of a neural respiratory drive (NRD).

Further optionally, a flow signal 37 indicative of a respiratory flow, for example measured by a nasal cannula, can be provided as a second input to the processing apparatus 10. The flow signal 37 can be provided to a respiration phase detection unit 15 which is configured to determine a respiratory phase and to provide a respiratory phase signal 38 as its output. The signal can be provided together with the RMS power signal 36 to an analysis unit 16 which can be configured to determine a respiratory effort during a desired respiratory phase, for example an inspiratory effort of the subject 100, and provide a clinical EMG parameter 39 at its output. This parameter can be powerful indicator for a physician. The amount of respiratory effort due to quiet breathing, in particular during the inhalation-phase, can be an important vital sign, for example, for the detection of exacerbation for COPD patients in the hospital or the home.

In conclusion, the concepts discussed herein can further improve the processing of a physiological signal. The proposed arrangement of a model subtraction unit 11 followed by a filter unit 12 and a subsequent gating unit 13 can reduce a first and a second unwanted signal component and advantageously further reduce the impact of artifacts that are generated by the signal processing itself.

It is to be understood that the proposed processing apparatus can also be implemented for example by a microcontroller, digital signal processor, field-programmable-gate-array (FPGA) or general purpose processor carrying out the method described herein.

The term "unit" as used herein shall be understood as a functional unit or entity that can be implemented in many different ways. In particular, the term unit shall not be limited to the exemplary embodiments disclosed herein. For instance, the respective functionality can be provided by one or more processing apparatuses or processors which are configured to act as a respective (functional) unit such as e.g. a model subtraction unit, a filter unit or gating unit. In other words, reference can also be made to a processing device configured to perform the functionalities of one or more of said (functional) units.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A processing apparatus for recovering a physiological signal from a signal that includes components that are not a part of the physiological signal, the processing apparatus comprising:
   a model subtraction circuit connected to an input to receive the signal and to reduce a first unwanted signal component in the signal by subtracting from the signal a model of the first unwanted signal component to produce a residual signal at an output of the model subtraction circuit;
   a filter circuit connected to the output of the model subtraction circuit to receive the residual signal from the model subtraction circuit and to reduce a second unwanted signal component in the residual signal by applying a notch filter to produce a filtered signal at an output to the filter circuit; and
   a gating circuit connected to the output of the filter circuit to receive the filtered signal from the filter circuit and to apply gating to the filtered signal to recover the recovered physiological signal; wherein the gating circuit is configured to selectively pass the filtered signal on to an output of the gating circuit as the recovered physiological signal.

2. The processing apparatus according to claim 1, wherein the processing apparatus is configured to recover an electromyography (EMG) signal as the recovered physiological signal.

3. The processing apparatus according to claim 1, wherein the model subtraction circuit is configured to reduce, as the first unwanted signal component, an electrocardiography (ECG) signal component comprised in the signal.

4. The processing apparatus according to claim 1, wherein the filter circuit is configured to reduce, as the second unwanted signal component, a power line signal component comprised in the signal.

5. The processing apparatus according to claim 1, wherein the model subtraction circuit is configured to determine the model of the first unwanted signal component from a plurality of cycles of the first unwanted signal component.

6. The processing apparatus according to claim 1, wherein said model of the first unwanted signal component comprises a waveform indicative of the first unwanted signal component.

7. The processing apparatus according to claim 1, wherein the gating circuit is configured to cap the filtered signal when a value indicative of the filtered signal exceeds a predetermined threshold (Th).

8. The processing apparatus according to claim 1, wherein the gating circuit is configured to cap the filtered signal when a value indicative of the model of the first unwanted signal component exceeds a predetermined threshold (Th).

9. The processing apparatus according to claim 8, wherein said threshold (Th) is an adaptive threshold based on a median root-mean-square value of the model of the first unwanted signal component.

10. The processing apparatus according to claim 8, wherein said threshold (Th) is an adaptive threshold based on a quality criterion indicative of a match between at least a part of the model of the first unwanted signal component and the signal.

11. The processing apparatus according to claim 1, wherein the gating circuit is configured to apply a binary mask of gate-regions to the filtered signal to further reduce the first unwanted signal component.

12. The processing apparatus according to claim 11, wherein the gating circuit is configured to reconstruct the filtered signal in a gate-region based on a signal level of the filtered signal before and/or after the gate-region.

13. An electromyography system comprising:
   two electrodes for application to a skin of a subject for acquisition of a physiological signal; and
   the signal processing apparatus for recovering said physiological signal as claimed in claim 1.

14. A method for recovering a physiological signal from a signal that includes components that are not a part of the physiological signal using a model subtraction circuit with an output connected to an input of a filter circuit, wherein an output of the filter circuit is connected to an input of a gating circuit, said method comprising acts of:
   receiving the signal at an input of the model subtraction circuit;
   reducing, by the model subtraction circuit, a first unwanted signal component in the signal by subtracting from the signal a model of the first unwanted signal component to obtain produce a residual signal at the output of the model subtraction unit;
   subsequently reducing a second unwanted signal component in the residual signal by the filter circuit applying notch filtering to produce a filtered signal at the output of the filter circuit; and
   subsequently applying gating, by the gating circuit, to the filtered signal to obtain produce a gated signal at an output of the gating circuit; wherein the gating comprises selectively passing on the filtered signal to the output of the gating circuit as the recovered physiological signal.

15. A non-transitory computer readable medium containing a computer program comprising program code for causing a computer to carry out the acts of the method as claimed in claim 14 when said computer program is carried out on the computer.

16. A processing system for recovering a physiological signal from a signal that includes components that are not a part of the physiological signal, the processing system comprising:

a model subtraction circuit connected to an input to receive the signal and to reduce a first unwanted signal component in the signal by subtracting from the signal a model of the first unwanted signal component to produce a residual signal at an output of the model subtraction circuit;

a filter circuit connected to the output of the model subtraction circuit to receive the residual signal from the model subtraction circuit and to reduce a second unwanted signal component in the residual signal by applying a notch filter to produce a filtered signal at an output of the filter circuit; and a gating circuit connected to the output of the filter circuit to receive the filtered signal from the filter circuit and to apply gating to the filtered signal to recover the recovered physiological signal; wherein the gating circuit is configured to selectively pass the filtered signal on to an output of the gating circuit as the recovered physiological signal, wherein the gating circuit is configured to cap the filtered signal when a value indicative of the model of the first unwanted signal component exceeds an adaptive threshold based on a quality criterion indicative of a match between at least a part of the model of the first unwanted signal component and the signal.

17. A processing system for recovering a physiological signal from a signal that includes components that are not a part of the physiological signal, the processing system comprising:

a model subtraction circuit connected to an input to receive the signal and to reduce a first unwanted signal component in the signal by subtracting from the signal a model of the first unwanted signal component to produce a residual signal at an output of the model subtraction circuit;

a filter circuit connected to the output of the model subtraction circuit to receive the residual signal from the model subtraction circuit and to reduce a second unwanted signal component in the residual signal by applying a notch filter to produce a filtered signal at an output of the filter circuit; and a gating circuit connected to the output of the filter circuit to receive the filtered signal from the filter circuit and to apply gating to the filtered signal to recover the recovered physiological signal; wherein the gating circuit is configured to selectively pass the filtered signal on to an output of the gating circuit as the recovered physiological signal, wherein the gating circuit is configured to apply a binary mask of gate-regions to the filtered signal to further reduce the first unwanted signal component.

18. The processing system according to claim 17, wherein the gating circuit is configured to reconstruct the filtered signal in a gate-region based on a signal level of the filtered signal before and/or after the gate-region.

* * * * *